US008693751B2

(12) United States Patent
Osborne et al.

(10) Patent No.: US 8,693,751 B2
(45) Date of Patent: *Apr. 8, 2014

(54) ARTIFICIAL INTELLIGENCE SYSTEM FOR GENETIC ANALYSIS

(75) Inventors: Glenn F. Osborne, Davis, CA (US); Simon S. M. Chin, Saratoga, CA (US); Paul McDonald, Saratoga, CA (US); Scott Schneider, Saratoga, CA (US)

(73) Assignee: Iris BioTechnology Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/349,225

(22) Filed: Jan. 12, 2012

(65) Prior Publication Data

US 2012/0177261 A1    Jul. 12, 2012

Related U.S. Application Data

(63) Continuation of application No. 11/399,733, filed on Apr. 7, 2006, now Pat. No. 8,107,693, which is a continuation of application No. 09/650,005, filed on Aug. 28, 2000, now Pat. No. 7,062,076.

(60) Provisional application No. 60/151,258, filed on Aug. 27, 1999.

(51) Int. Cl.
*G06K 9/00* (2006.01)

(52) U.S. Cl.
USPC ........................................................ 382/128

(58) Field of Classification Search
USPC ........................................................ 382/128
See application file for complete search history.

(56) References Cited

U.S. PATENT DOCUMENTS 4,817,050 A    3/1989 Komatsu et al.

5,239,060 A * 8/1993 Kunkel et al. ............... 530/350

(Continued)

FOREIGN PATENT DOCUMENTS

| WO | WO 97/20496 | 6/1997 |
|----|-------------|--------|
| WO | WO 98/26407 | 6/1998 |

(Continued)

OTHER PUBLICATIONS

Eckman et at "The Merck Gene Index browser: an extensible data integration system for gene finding, gene characterization and EST data mining" Bioinformatics, GB, Oxford University Press, 14(1): 2-13 (1998).

(Continued)

*Primary Examiner* — Tom Y Lu
(74) *Attorney, Agent, or Firm* — Fenwick & West LLP (57) ABSTRACT

The present invention provides a complete artificial intelligence system for the acquisition and analysis of nucleic acid array hybridization information. The system includes a central data processing facility and one or more user facilities, linked by encrypted connections. Each user facility may include an optical scanning system to collect hybridization signals from a nucleic acid array, an image processing system to convert the optical data into a set of hybridization parameters, a connection to a data network, and a user interface to display, manipulate, search, and analyze hybridization information. This system reads data from a nucleic acid microarray, analyzes test results, evaluates patient risk for various ailments, and recommends methods of treatment. The automated artificial intelligence system is a real time, dynamic decision making tool that can be used in conjunction with a clinical analysis system, and with the information obtained in a research and development environment.

35 Claims, 3 Drawing Sheets

System Architecture

(56) References Cited

U.S. PATENT DOCUMENTS

| | | | |
|---|---|---|---|
| 5,692,107 | A | 11/1997 | Simoudis et al. |
| 5,733,729 | A | 3/1998 | Lipshutz et al. |
| 5,769,074 | A | 6/1998 | Barnhill et al. |
| 5,779,634 | A | 7/1998 | Ema et al. |
| 5,837,832 | A | 11/1998 | Chee et al. |
| 5,839,438 | A | 11/1998 | Graettinger et al. |
| 5,861,242 | A | 1/1999 | Chee et al. |
| 5,878,746 | A | 3/1999 | Lemelson et al. |
| 5,911,687 | A | 6/1999 | Sato et al. |
| 5,936,078 | A | 8/1999 | Kuga et al. |
| 5,966,712 | A | 10/1999 | Sabatini et al. |
| 5,970,500 | A | 10/1999 | Sabatini et al. |
| 5,981,185 | A | 11/1999 | Matson et al. |
| 6,004,755 | A | 12/1999 | Wang |
| 6,040,138 | A | 3/2000 | Lockhart et al. |
| 6,063,026 | A | 5/2000 | Schauss et al. |
| 6,083,726 | A | 7/2000 | Mills, Jr. et al. |
| 6,087,112 | A | 7/2000 | Dale |
| 6,107,073 | A * | 8/2000 | Chen ............................ 435/194 |
| 6,136,541 | A | 10/2000 | Gulati |
| 6,263,287 | B1 | 7/2001 | Zheng et al. |
| 6,338,968 | B1 | 1/2002 | Hefti |
| 7,062,076 | B1 | 6/2006 | Osborne et al. |

FOREIGN PATENT DOCUMENTS

| | | | |
|---|---|---|---|
| WO | WO 98/37187 A1 | 8/1998 | |
| WO | WO 98/49647 | 11/1998 | |
| WO | WO 99/04043 | 1/1999 | |
| WO | WO 99/05323 A1 | 2/1999 | |
| WO | WO 99/05591 | 5/1999 | |
| WO | WO 99/41373 | 8/1999 | |
| WO | WO 99/63886 | 12/1999 | |
| WO | WO 00/28080 | 5/2000 | |
| WO | WO 00/28091 | 5/2000 | |
| WO | WO 00/29983 | 5/2000 | |
| WO | WO 00/41613 | 7/2000 | |

OTHER PUBLICATIONS

Cristea, et al. Proteomics techniques and their application to hematology, Blood 103(10): 3624-3634, (2004).

Ray et al., "Peptide nucleic acid (PNA): its medical and biotechnical applications and promise for the future", FASEB J 14: 1041-1060, (2000).

Chou, et al., "Optimization of probe length and the number of probes per gene for optimal micoarray analysis of gene expression", Nucleic Acids Research, vol. 32, No. 12., e99, pp. 1-8, (2004).

Kothapalli et al., Microarray results: how accurate are they?, BMC Bioinformatics, 3: pp. 22-23, (2002).

Relogio et al., "Optimization of oligonucleotide-based DNA microarrays", Oxford University Press, Nucleic Acids Research, vol. 30, No. 11., e51, pp. 1-10, (2002).

Chen, et al., "Covalent Attachment of Sequence-optimized PCR Products and Oligos for DNA Microarrays", Operon Technologies, Inc.

Japanese Patent Office, Official Action, Japanese Patent Application No. JP 2001-520734, Oct. 30, 2012, twenty-four pages.

Japanese Patent Office, Official Action, Japanese Patent Application No. JP 2011-133605, Mar. 19, 2013, five pages.

PCT International Search Report, PCT Application No. PCT/US2000/023597, Mar. 23, 2001, five pages.

Akutsu, T., "DNA Chips and Gene Network," *Exploration of Life Principle from Genome Information, BIT Computer Science Journal*, Jun. 1, 1999, pp. 13-17, vol. 31, No. 6.

Hayashi, K., "The leading edge of human genome research in Japan: Diversification of Human Genome," *Genome Science: Toward the Complete Understanding of the Genetic Blueprint of Life*, Dec. 1997, pp. 2976-2980, vol. 42, No. 17.

Japanese Patent Office, Office Action, Japanese Patent Application No. 2011-133605, Oct. 8, 2013, six pages.

\* cited by examiner

Figure 1: System Architecture

Figure 2: System Design

Figure 3: System Scaling

ARTIFICIAL INTELLIGENCE SYSTEM FOR GENETIC ANALYSIS

CROSS REFERENCE TO RELATED APPLICATIONS

This application is a continuation of, and claims priority under 35 U.S.C. §120 to, U.S. application Ser. No. 11/399,733 filed Apr. 7, 2006 now U.S. Pat. No. 8,107,693, which is a continuation of, and claims priority under 35 U.S.C. §120 to, U.S. application Ser. No. 09/650,005 filed Aug. 28, 2000 now U.S. Pat. No. 7,062,076, which claims the benefit under 35 U.S.C. §119(e) of U.S. Provisional Application Ser. No. 60/151,258, filed Aug. 27, 1999, the entire contents of which applications are hereby incorporated by reference in their entirety.

FIELD OF THE INVENTION

The present invention relates to electronic genetic analysis systems, and more particularly, to a computerized artificial intelligence system for acquiring and processing DNA hybridization patterns and comparing the processed patterns with databases for clinical or research applications.

BACKGROUND OF THE INVENTION

Nucleic acid analysis can provide important diagnostic and prognostic information in both clinical and research environments. With amplification techniques such as the polymerase chain reaction, routine clinical samples can provide material for extensive genetic analysis of known traits. For example, the drug resistance characteristics of a pathogen can be determined by genomic analysis if the sequence of genes or mutations conferring drug resistance is known. Knowledge of drug resistances allows design of an appropriate therapy. Similarly, screening for known mutations in cellular oncogenes can diagnose or direct the treatment of cancer.

The advent of high-density nucleic acid hybridization devices, generally known as "DNA chips" or "nucleic acid arrays", has greatly extended the range of possible clinical applications for nucleic acid analysis. The ability to perform simultaneously millions of nucleic acid hybridization experiments makes feasible large-scale screening assays on a single clinical sample. For example, in U.S. Pat. No. 5,861,242, Chee et al. disclose DNA arrays designed to determine the complete nucleotide sequence of a segment of the HIV genome where mutations in the viral reverse transcriptase gene correlate with drug resistant phenotypes. Combined with appropriate amplification techniques, nucleic acid arrays bearing a battery of probes complementary to pathogen genomes can be used to rapidly screen clinical or industrial samples for hundreds or thousands of mutations, pathogens or contaminants.

Another application of high density nucleic acid arrays is in profiling the genomic expression pattern of an organism. By measuring the degree of hybridization of an RNA sample to an array of nucleic acid probes, each corresponding to a transcribed segment of the genome, it is possible to simultaneously assess the expression level of many or all of the genes of an organism. In U.S. Pat. No. 6,040,138, Lockhart et al. describe methods of monitoring the expression levels of a multiplicity of genes, wherein a high density array contains oligonucleotide probes complementary to target nucleic acids, including RNA transcripts. The arrays are used to detect the presence or absence of target nucleic acid sequences, and to quantify the relative abundance of the target sequences in a complex nucleic acid pool. Small variations in expression levels of a particular gene can be identified and quantified in a complex population of genes that outnumber the target nucleic acids by a million fold or more. In U.S. Pat. No. 6,004,755, Wang et al. describe quantitative microarray hybridization assays, wherein end-labeled target nucleic acids are contacted with an array of probe molecules stably associated with the surface of a solid support under hybridization conditions. The resulting hybridization pattern can be used to obtain quantitative information about the genetic profile of the end-labeled target nucleic acid sample and the source from which it is derived.

Computer systems and electronic databases for the analysis of biological information are known in the art. Several types of electronic databases are currently available, including genomic databases, medical diagnostic analysis systems, and clinical information systems. U.S. Pat. No. 5,966,712 encompasses a relational database system for storing and manipulating biomolecular sequence information, including genomic libraries for different types of organisms. Comparative Genomics is a feature of this database system which allows a user to compare the sequence data sets of different organism types. U.S. Pat. No. 6,063,026 describes a computerized medical diagnostic method, including a database containing diseases and indicators associated with each disease, and a second database containing human test results associated with each indicator. An individual's test results are compared with the second database to determine presence levels of each indicator to ultimately provide a medical analysis of the individual and identify therapeutic treatments and drugs. The method is based on pattern matching of diseases associated with the various indicator presence levels. PCT publication WO 99/04043 discloses Telemedicine, a computer system that provides for automatic test tracking and analysis. Test results and patient profile medical history can be inputted into the system or network and compared with databases of diseases, disorders, treatments, care plans, nutritional supplements, and medicine. This system can transmit an analysis and proposed treatment to the patient's physician or health care provider for approval before it is sent to the patient. This system is also used for automatic test tracking and reporting to public health organizations.

Advances in the genomics and bioinformatics area, especially the development of gene chips and micro arrays, require more and more sophisticated bioinformatics tools for the manipulation and analysis of gene expression data. Thus, attempts have been made to provide systems that simplify the analysis of micro array expression data. For example, PCT publication WO 00/28091 describes a system and integrated computer software programs for the manipulation and analysis of gene expression data, particularly suited for expression data generated with micro array technologies. This system includes graphical tools, search and sort functions for viewing gene expression data, as well as a graphical user interface for data clustering, browsing, and viewing. U.S. Pat. No. 5,733,729 discloses a computer system for analyzing nucleic acid sequences, wherein the system is used to calculate probabilities for determining unknown bases by analyzing the fluorescence intensities of hybridized nucleic acid probes on biological chips. This system uses information from multiple experiments to improve the accuracy of calling unknown bases.

As of today, no electronic system has yet been devised wherein nucleic acid expression patterns derived from high density arrays can be analyzed, stored, manipulated, and compared; and then linked to patient profiles, medical conditions, and treatments of various ailments and diseases. Such a system would combine experimental hybridization data analysis and clinical applications. If a database of gene expression patterns reflecting distinct pathological or physiological states of the sampled tissue exists, comparison of the sample's gene expression profile with stored gene expression profiles can provide important information about the biological state of the tissue. Such information could be used to assess a variety of biological states of interest, such as neoplasia, cancer, immune response, environmental stress or nutritional condition, and the like. Such information could further be used to provide appropriate treatment for a variety of pathological conditions, ailments, and diseases.

The object of the present invention is to provide a system where nucleic acid array hybridization information is compared with a central repository of hybridization profiles to provide medical, experimental, or industrial analysis of biological samples. Another object of the present invention is to provide a system where analyzed nucleic acid array hybridization information can be linked and correlated to patient profiles, medical conditions, and treatments of various ailments and diseases. Publications, patents, and other reference materials referred to herein are incorporated herein by reference.

SUMMARY OF THE INVENTION

The present invention provides a complete system for the acquisition and analysis of nucleic acid array hybridization information in combination with a clinical analysis system and databank. This automated artificial intelligence system encompasses monitoring, screening, diagnosing, and performing prognosis of disease(s) and condition(s) by integrating primary and secondary genomic information, patient profiles, animals and crops information, insects and other living organism profiles, and disease models, using proprietary neural network algorithms. The resulting information can be used for patient treatment analysis as well as for research and development, particularly drug discovery. In addition, the system links internal and external clinical and research data bases; processes information in real-time; uses the Internet and other wireless technologies to transmit or receive information; provides access to information that is useful in managing disease outbreaks and emergency situations; provides tiered information access to doctors, patients, researchers, and others; performs simultaneous, multi-dimensional analysis; and analyzes genetic information by ethnicity, region, occupation, age, sex, and the like. The automated artificial intelligence system is a real time, dynamic decision making tool that can be used not only in conjunction with a clinical analysis system, but also with the information obtained in a research and development environment. Access to this system allows the user(s) to look at both clinical and non-clinical information. Most importantly, the system is intelligent and possesses the capability to interpret the information obtained.

The system is divided into at least one central data processing facility and one or more user facilities, linked by encrypted network connections or similar links. Each user facility may include an optical scanning system to collect hybridization signals from a nucleic acid array, an image processing system to convert the optical data into a set of hybridization parameters, a connection to a data network, and a user interface to display, manipulate, search, and analyze hybridization information. Alternatively, the optical scanning system may collect signals from a proteomics array or chip, and the image processing system may convert the optical data into a set of proteomics parameters. The user interface may be used to display, manipulate, search, and analyze proteomics related information.

One aspect of the present invention provides at least one central data processing facility, including a Web server or other mechanism (e.g., Electronic Data Interchange (EDI), Dial-Up, etc.) that communicates with remote user facilities, receiving and transmitting hybridization information, and supports data analyses, as well as providing security and business functions. The central data processing facility further includes a database server that stores hybridization profiles, patient profiles, reference information, clinical information associated with hybridization profiles, statistical summaries, and the like. Mediating between the Web server and the database server is an application server, which constructs queries for the database server and performs statistical comparisons between hybridization parameters received by the Web server and hybridization parameters supplied by the database server.

In one manner of practicing the invention, clinicians and other laboratory personnel, utilizing a nucleic acid array, collect hybridization information from a clinical sample and transmit this information to a central data processing facility along with the identity of the array. At the central data processing facility, the hybridization profile is compared with stored hybridization parameters, and artificial intelligence routines determine the most likely pathological or physiological conditions suggested by the hybridization information. These possibilities, along with suggested methods of treatment for the conditions, are returned to the user. The suggested methods of treatment may be chosen simply by reference to the indicated pathological or physiological condition, or may be chosen for likely therapeutic effectiveness based on particular hybridization parameters. In an alternative manner of practicing the invention, a proteomics chip may be used instead of a nucleic acid array.

In some manners of practicing the invention, hybridization profiles collected by remote and/or local facilities include clinical observations or other information associated with each profile, and the profile with its associated observations is added to the central database. In other manners of practicing the invention, hybridization profiles submitted to the central facility do not contain associated observations and are not added to the central database.

In another manner of practicing the invention, users perform statistical tests on cataloged hybridization profiles stored in the central data processing facility. By correlating the hybridization signal of one or more probes in the array with clinical information recorded for each hybridization profile, users create and test hypotheses relating hybridization information to particular pathological or physiological states. A variety of statistical analyses are provided to suggest and evaluate hypotheses.

BRIEF DESCRIPTION OF THE FIGURES

The present invention is best understood when read in conjunction with the accompanying figures that serve to illustrate the preferred embodiments. It is understood, however, that the invention is not limited to the specific embodiments disclosed in the figures.

FIG. 1 provides a flow chart of the artificial intelligence system and its architecture. The system is divided into at least one central data processing facility and one or more user facilities, linked by encrypted network connections or similar links. The central data processing facility includes a Web Server or other mechanism (e.g., Electronic Data Interchange (EDI), Dial-Up, etc.), Application Server, Database Server, and Operations Server. For the purpose of illustrating the instant invention, a remote user facility is depicted, including a Diagnostic User entity and a Browse User entity.

FIG. 1 depicts the flow of information between the server nodes, such as the Web Server, Application Server, Database Server, and Operations Server, wherein the information flows back and forth within the central data processing facility as shown by black connecting lines. FIG. 1 further depicts the flow of information between a remote user facility and the central data processing facility, wherein information flows back and forth between the Diagnostic User entity and the Web Server, as well as the Browse User entity and the Web Server.

FIG. 1 also depicts the various functionalities within each server node in the central data processing facility. The Web server includes, but is not limited to, security functionality, products and company description, statistical summary of patient database, request to application server, and product ordering. The Application Server includes, but is not limited to, database (DB) query for chip identifier (ID), DB query for statistical data summary, pattern match statistical processing, and sending results to DB and back to user functionality. The Database Server includes, but is not limited to, genetic pattern DB for all chip ID, patient genetic pattern DB, and statistical data summary. The Operations Server includes, but is not limited to, order management, billing management, and order tracking.

FIG. 1 also depicts the various functionalities within each entity in the user facility. The Diagnostic User entity includes, but is not limited to, a DNA microarray or gene chip, an array or chip scanner, a PC system, a user interface for system operations, a genetic pattern processing functionality, request for pattern match for chip ID to central processing facility, and a report generation functionality.

DETAILED DESCRIPTION OF THE INVENTION a) Definitions and General Parameters

The following definitions are set forth to illustrate and define the meaning and scope of 15 the various terms used to describe the invention herein.

A "polynucleotide", "oligonucleotide", or "nucleic acid" includes, but is not limited to, mRNA, cDNA, genomic DNA, and synthetic DNA and RNA sequences, comprising the natural nucleotide bases adenine, guanine, cytosine, thymine, and uracil. The terms also encompass sequences having one or more modified nucleotide(s). The terms "polynucleotide" and "oligonucleotide" are used interchangeably herein. No limitation as to length or to synthetic origin are suggested by the use of either of these terms herein.

A "probe" is a nucleic acid sequence, optionally tethered, affixed, or bound to a solid surface such as a microarray or chip.

A "target nucleic acid" is generally a free nucleic acid sample whose identity or/and abundance can be detected through the use of a DNA micro array.

The term "sequences which hybridize thereto" means polynucleotide sequences which are capable of forming Watson-Crick hydrogen bonds with another polynucleotide sequence or probe that is bound to an array or chip. Although the sequences which hybridize to a polynucleotide or probe may be about 90%-100% complementary to the polynucleotide or probe, if the sequences are of sufficient length, in solutions with high salt concentrations, and/or under low temperature conditions, polynucleotides with complementarily of 70% or above, or even just 50% or above, may-hybridize to the polynucleotide or probe.

The terms "gene chip", "DNA microarray", "nucleic acid array", and "gene array" are used interchangeably herein. These terms refer to a solid substrate, generally made of glass but sometimes made of nylon or other materials, to which probes with known identity are bound. The probes can hybridize to target nucleic acids through complementary binding, thus allowing parallel gene expression and gene discovery studies. Variants of DNA microarray technology are known in the art. For example, cDNA probes of about 500 to about 5,000 bases long can be immobilized to a solid surface such as glass using robot spotting and exposed to a set of targets either separately or in a mixture. Alternatively, an array of oligonucleotides of about 20 mer to about 25 mer or longer oligos or peptide nucleic acid (PNA) probes is synthesized either in situ (on-chip) or by conventional synthesis followed by on-chip immobilization. The array is exposed to labeled sample DNA, hybridized, and the identity and/or abundance of complementary sequences is determined.

The term "proteomics" is most broadly defined as the systematic analysis and documentation of proteins in biological samples. Proteomics is a mass-screening approach to molecular biology, which aims to document the overall distribution of proteins in cells, identify and characterize individual proteins of interest, and ultimately, elucidate their relationships and functional roles. The term "proteomics chip" or proteomics array" refers to a solid substrate to which proteins with known identity are bound.

A "clinical sample" or "biological sample" may be a sample of tissue or a sample of body fluid. The term "tissue" is used herein to refer to any biological matter made up of one cell, multiple cells, an agglomeration of cells, or an entire organ. The term tissue, as used herein, encompasses a cell or cells which can be either normal or abnormal (i.e. a tumor). A "body fluid" may be any liquid substance extracted, excreted, or secreted from an organism or a tissue of an organism. The body fluid need not necessarily contain cells. Body fluids of relevance to the present invention include, but are not limited to, whole blood, serum, plasma, urine, cerebral spinal fluid, tears, and amniotic fluid.

b) The Artificial Intelligence System

The present invention provides a complete artificial intelligence system for the acquisition and analysis of high-density and low-density nucleic acid array hybridization information. This system reads data from a gene chip or DNA microarray, analyzes test results based on maintained parameters, evaluates patient risk for various ailments, recommends methods of treatment, presents information to medical and/or private individuals, and notifies test participants when new treatment becomes available. The system captures data from a gene chip and stores test results in a database using an optical scanning methodology. Gene chips are controlled by using a unique inventory identifier (ID). Correlated data may be collected by the medical practitioner or researcher and entered into the system via an electronic interface, in order to provide additional information that may be used in various analyses. The test results may be used to perform individual diagnostics, longitudinal studies, population studies, or a wide variety of statistical analyses of patient data. The system also has embedded and/or linked software for planning, manufacturing, quality assurance, processing, and tracking its microarray products. Furthermore, the system presents the information primarily via a secured encrypted Web interface, such as the Internet. The information is also presented in a retrievable format, such as electronic or paper format, using various computing technologies.

The artificial intelligence system allows for clinical, research and development related genetic testing. This system involves the use of microarray technology in the form of a DNA chip in conjunction with a fluidics station, chemical reagents, chemical fluorescence and an optical reader or scanner system. Genetic testing is performed by using chemical reagents to extract the DNA or RNA from a biological sample. Subsequently the prepared sample is applied to the DNA chip via the fluidics station. A DNA chip has a large number of spots, each of which corresponds to a specific nucleic acid sequence (e.g., nucleic acid probe, genomic DNA, cDNA, etc.). The extent to which the hybridized DNA or RNA attaches to each spot on the chip indicates the level at which a specific gene is expressed in the sample. Using the optical reader or scanner to image the hybridized DNA microarray can provide the means to quantify the gene expression levels for each spot. Image processing software, hosted in the PC attached to the optical reader or scanner, operates on the raw image data to generate an optical intensity measurement for each spot for each fluorescent color used in the test. This indicates the "brightness or light intensity" of the spot for each fluorescent color and the expression level for the gene sequence corresponding to that spot. The artificial intelligence system or a linked software program converts the gene expression data to test results data directly applicable to the clinical or research and development associated user. These test results include diagnosed medical and/or clinical conditions for clinical users, and the system also provides an associated set of treatment options for the diagnosed clinical conditions.

Figure 1:
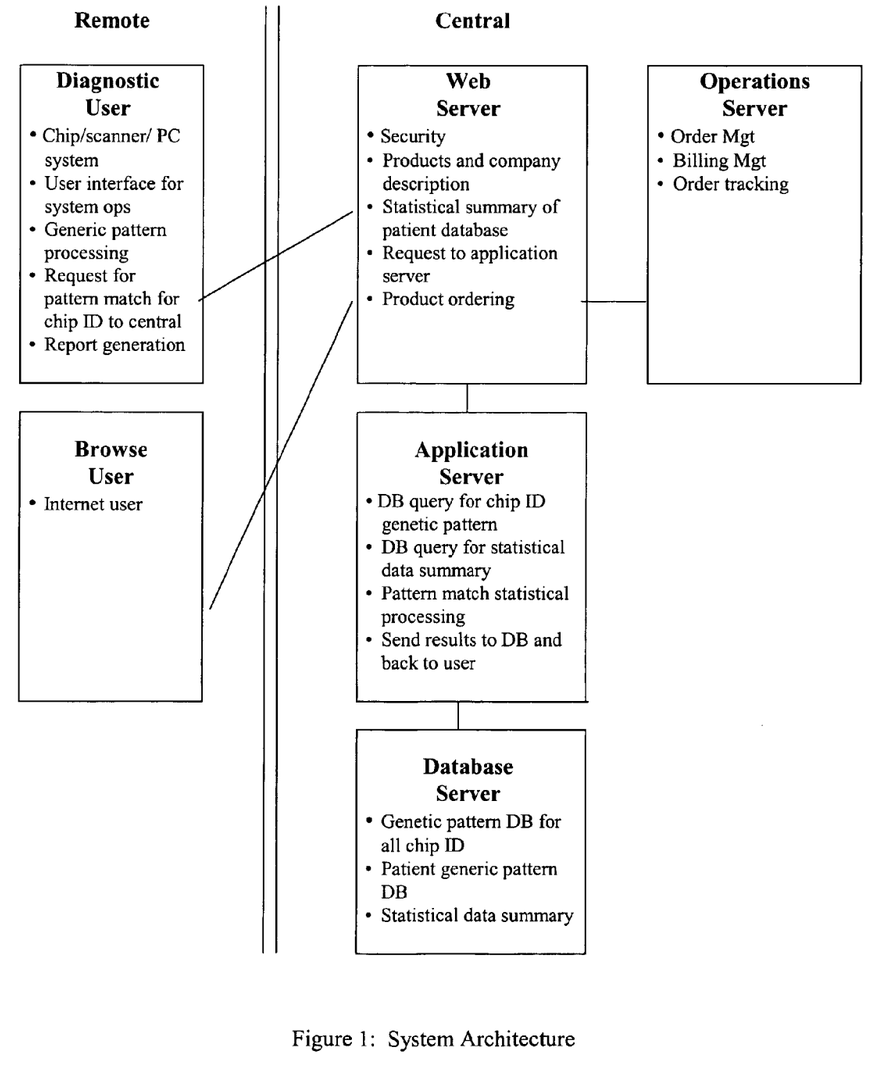
Figure 2:
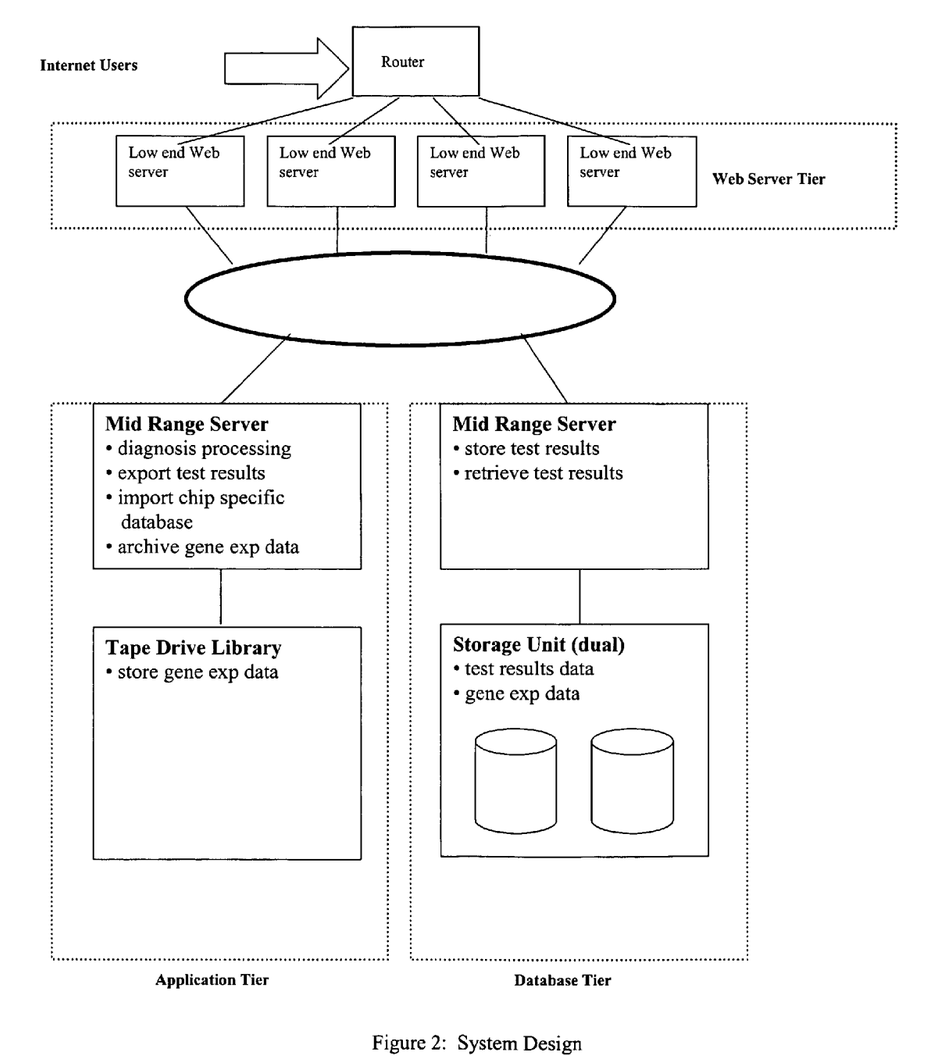
FIG. 2 shows a possible schematic representation of the system design of the automated artificial intelligence system, including a Web Server Tier, Application Tier, and Database Tier.
Figure 3:
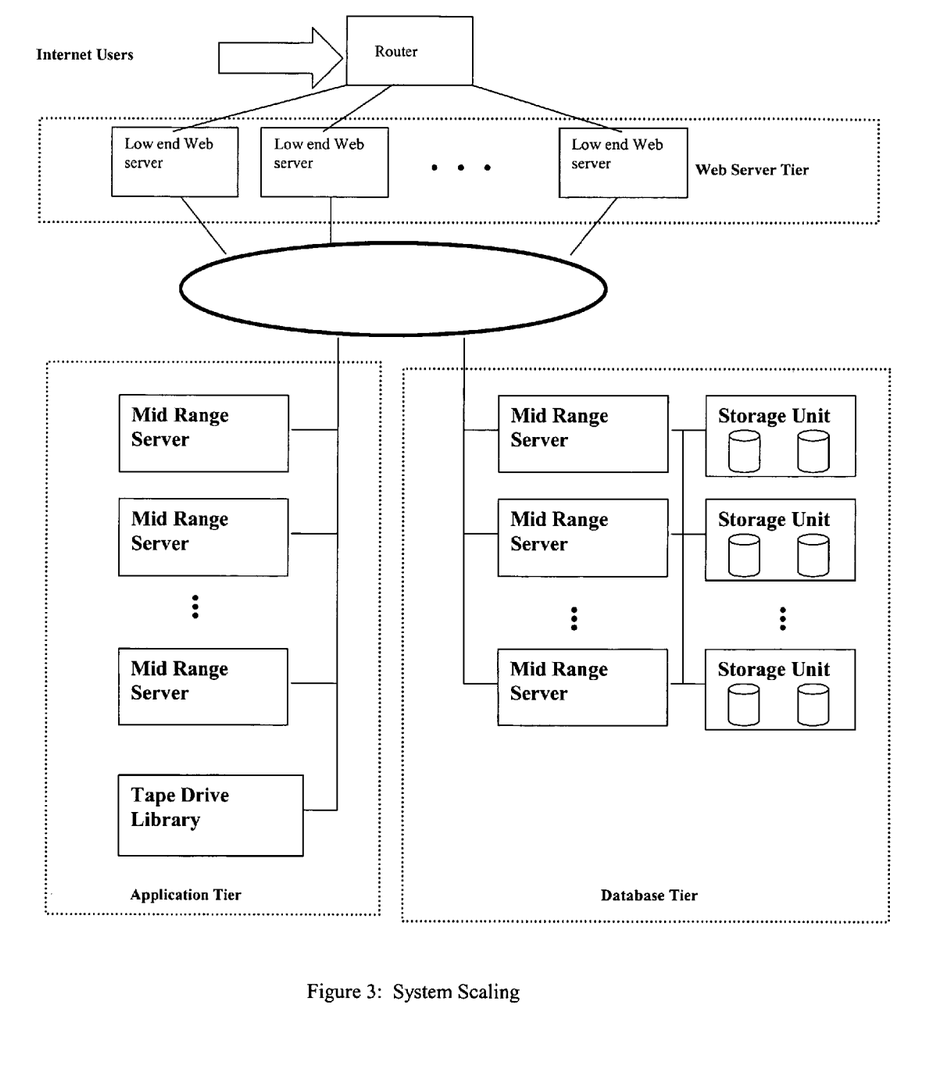
FIG. 3 shows a possible schematic representation of the system scaling, including a Web Server Tier, Application Tier, and Database Tier.

The artificial intelligence system is divided into at least one central data processing facility and one or more remote and/or local user facilities, linked by encrypted network connections or similar links. The architecture of this system is based on a shared processing functionality between remote or local user facilities including, but not limited to, hospitals, clinics, research facilities, businesses, and non-profit organizations; and a central location, such as a company centralized location. The remote or local user facilities also include a Web user or Internet user who requests information or orders products. FIG. 1 displays the system architecture of the instant invention. FIGS. 2 and 3 depict the system design and scaling, respectively, relating to the application tier and database tier.

In a preferred embodiment, each remote or local user facility includes an optical scanning system to collect hybridization signals from a nucleic acid array, an image processing system to convert the optical data into a set of hybridization parameters, a connection to the Internet or other data network, and a user interface to display, manipulate, search, and analyze hybridization information. A potentially large number of optical reader or scanner and PC systems may be deployed at user sites throughout the world. In an alternative embodiment, each remote or local user facility includes a connection to the Internet or other data network, and a user interface to manipulate, search, analyze, and display data (e.g., hybridization information, patient information, statistical information, clinical and medical information, diagnosis and treatment information, biological information, product information, company information, etc). The artificial intelligence system provides Internet access to diagnosis processing and associated treatment information. The remote or local user facility comprises a diagnostic user (e.g., hospital, clinic, research facility, business, non-profit organization, and the like) and a browse user (e.g., Internet user). The diagnostic user utilizes the system, including the fluidic station to use gene chips or DNA microarrays, the scanner and/or detector to read the chip data, the memory storage to store the scanned chip data, and a PC or other desktop system to search, display, correlate, manipulate, and analyze data via a user interface. The memory storage can be located directly in the scanner system. But the chip data may also be stored in the PC associated with the scanner, or in both, the scanner system and desktop system.

In an alternative embodiment, the optical scanning system may collect signals from a proteomics array or chip, and the image processing system may convert the optical data into a set of proteomics parameters. The user interface may be used to display, manipulate, search, and analyze proteomics related information. More specifically, information (e.g., signals) may be collected from a proteomics chip, transmitted to the central data processing facility, analyzed to generate a proteomics profile, and compared to stored proteomics parameters to provide analyzed data. The analyzed data can then be used to determine physiological condition through the use of artificial intelligence. Methods of treatment based on the physiological condition(s) may be recommended.

Gene expression analysis and other specific, less comprehensive hybridization profile analysis can be performed in the remote or local user facility which allows the system to be a stand alone system and it simplifies the interface to the central system. Alternatively, a chip may be scanned in the user facility resulting in raw scanned or preprocessed data which can then be sent to the central processing facility for further analysis. For example, a CD with raw data may be sent to the central processing facility where the data is analyzed. After further analysis, a genetic pattern emerges which can be compared and correlated to existing data and matched to the application in the central processing facility.

There are two categories of diagnostic users, such as "diagnostic master users" and "diagnostic users". Accounts for diagnostic master users are authorized and correspond to the user sites where the systems are deployed. These diagnostic master users are allowed to authorize accounts for diagnostic users. For clinical applications, diagnostic users correspond to the individuals that have been tested. For research and development applications, diagnostic master users can designate either individual chip test results or groups of chips as a single diagnostic user, wherein this option lies with the diagnostic master users in order to meet their testing and analysis needs.

Diagnosis processing is a key part of the artificial intelligence system. The diagnosis processing for clinical applications may be different from that of research and development applications. Diagnosis processing for clinical applications implements a rules based analysis application which utilizes a database set of rules and results. Diagnosis processing thereby determines which conditions apply to the various combinations of gene expression levels and personal medical history. For example, a cardiovascular chip for clinical applications may include a wide variety of spots with identified genomic mutations associated with various cardiovascular conditions. The diagnosis processing for this chip is based on the expression levels for each of these gene sequences, using predefined rules to determine the likelihood of a set of identified diseases or cancers. For example, the rules might be implemented as: If the gene sequences on spots 18, 52 and 115 have high expression levels, and if the gene sequences on spots 34, 88 and 125 have low expression levels, and the individual has a family history of heart disease, then this individual has a high likelihood of developing a specified heart disease within years. Additionally, there may be a database set of treatments developed for each diagnosed condition. As each chip may utilize at least several thousand spots, the database set of rules is complex. This type of processing is well suited to employ expert systems and/or rules based processing applications which are provided in the instant invention. The development of these database sets of rules and results include both, public information and private information. The databases of the instant invention continually mature and develop into more and more complex systems as information from public and private sources continues to be added to the existing databases.

Another aspect of the present invention provides at least one central data processing facility with dedicated servers for specific functions. The central data processing facility includes a Web server or other mechanism (e.g., Electronic Data Interchange (EDI), Dial-Up, etc.) that communicates with remote user facilities, receiving and transmitting hybridization information, and supports data analyses, as well as providing security and business functions. In particular, the Web server comprises functions including, but not limited to product information, product ordering, company information, statistical summary of patient database, request to the application server, and security. An overview of the artificial intelligence system is shown in FIGS. 1, 2 and 3. The central data processing facility further includes a database server that stores hybridization profiles, patient profiles, reference information, clinical information associated with hybridization profiles, various statistical summaries, and the like. More specifically, the database server comprises functions including, but not limited to genetic pattern database for chip ID, patient generic pattern database, and statistical data summary. Mediating between the Web server and the database server is an application server, which constructs queries for the database server and performs statistical comparisons between hybridization parameters received by the Web server and hybridization parameters supplied by the database server. In particular, the application server comprises functions including, but not limited to database query for chip ID genetic pattern, database query for statistical data summary, pattern match statistical processing, and results output. The central processing facility also includes an operations server wherein the operations server comprises functions such as order management, billing management, order tracking, and the like.

Another aspect of the present invention provides for a method, wherein clinicians and other laboratory personnel, utilizing a nucleic acid array, collect hybridization information from a clinical sample and transmit this information to a central data processing facility along with the identity of the array. In a preferred embodiment, the hybridization profile is compared with stored hybridization parameters at the central data processing facility, and artificial intelligence routines determine the most likely pathological or physiological conditions suggested by the hybridization information. These possibilities, along with suggested methods of treatment for the conditions, are returned to the user. In an alternative embodiment, the hybridization profile is compared with stored hybridization parameters at the user facility and raw scanned or preprocessed data is then sent to the central processing facility for further analysis. For example, a CD with raw data may be sent to the central processing facility where the data is analyzed via artificial intelligence. Results are returned to the user with suggested methods of treatment. The suggested methods of treatment may be chosen simply by reference to the indicated pathological or physiological condition, or may be chosen for likely therapeutic effectiveness based on particular hybridization parameters. In an alternative method of the instant invention, a proteomics array or chip may be used instead of a nucleic acid array.

In a manners of practicing the invention, hybridization profiles collected by remote and/or local facilities include clinical observations or other information associated with each profile, and the profile with its associated observations is added to the central database. In another manner of practicing the invention, hybridization profiles submitted to the central facility do not contain associated observations and are not added to the central database.

In yet another manner of practicing the invention, users perform statistical tests on cataloged hybridization profiles stored in the central data processing facility. By correlating the hybridization signal of one or more probes in the array with clinical information recorded for each hybridization profile, users create and test hypotheses relating to hybridization information to particular pathological or physiological states. A variety of statistical analyses are provided to suggest and evaluate hypotheses.

The instant invention also encompasses a method, wherein a Web user or browse user (e.g., Internet user), transmits existing processed. chip data, such as a hybridization profile, to the central data processing facility along with the identity of the profile. This may be done by directly supplying the data via a secure network connection, or by submitting the data via a CD, or the like. The hybridization profile is then compared with stored hybridization parameters at the central data processing facility, and artificial intelligence routines determine the most likely pathological or physiological conditions suggested by the profile supplied by the user. Accordingly, suggested methods of treatment for the conditions; are returned to the user.

In yet another method of the instant invention, a Web user or browse user may search the artificial intelligence system and view statistical summaries of the database. In this manner, a user would use the database to search, correlate, manipulate, and display existing data.

c) The System Architecture

A key feature of the artificial intelligence system is the archiving of all test data. All gene expression data that enters the system is both, used in diagnosis processing and archived for processing at a later time. Significant upgrades in the diagnosis processing database occur over time which changes the clinical meaning of any given set of gene expression data as new information is supplied to the system. The system repeatedly updates the existing information. For example, the clinical information based on a. gene expression data set may be different from one year to another as the information is continuously compared to new findings as a result of 30 data influx and developments and advances in research and medicine. The system has the capability to identify which archived data should be processed based on the diagnosis processing database history. In addition, the system has the ability to implement the reprocessing. Email notification of revised results may be sent to master users and users, whenever data has been updated or reprocessed.

Another key feature of the system is that it provides immediate access to all generated test results. Master users and users can view the entire history of all test results for a particular, related user. This is well suited to be a key feature for clinical users and associated clinicians and/or genetic counselors. This is also the mechanism through which new test results derived from reprocessing of archived gene expression data are available to any given user.

The system has two key databases for analysis of DNA chips. The first data base contains the probes (e.g., oligos such as 25 mer, 50 mer, 70 mer, or cDNA fragments, etc.) representing specific genes and the genes' sequences (e.g., full length cDNA). Thus, the first database encompasses the sequence tags for each spot on the chip. The gene targets for the sequence tags are defined by the genomics category and the bioinformatics category which process the specific sequence tags to be used in both chip production and clinical analysis of the test data. The second database is the diagnosis processing database which contains the hybridization profiles and provides the diagnosis of the test results. This database relies on artificial intelligence to analyze and interpret the gene expression data and other biological information (e.g., genomic deletions, additions, transcription, etc.). Hence, this database contains a set of rules for the various combinations of gene expression levels and the associated diagnosed conditions with associated treatment options. There is also an additional and optional diagnosis database that is used specifically for research and development related DNA chips.

The following section lists each element of the system, wherein the functionality and processing is defined in hierarchical form. This illustration provides an overview of the system architecture, including the server nodes and their associated functionality. An overview of the artificial intelligence system architecture is also shown in FIG. 1.

Diagnostic User Architecture
1.0 User commands
A. Application ID select
1.2 Initiate scan & processing
1.3 Output data
   1.3.1 Initiate transfer to central system for processing
   1.3.2 Report generation
2.0 Remote processing
2.1 Data management
   2.1.1 Memory search management
   2.1.2 Data transfer from scanner/detector system memory
2.2 Genetic pattern generation
   2.2.1 Single site pattern generation
   2.2.2 Aggregation to multi site result
2.3 Generate data format for export to central system
Central Data Processing Facility Architecture
1.0 Web Server
1.1 Security
   1.1.1 Browse user
   1.1.2 Product ordering user
   1.1.3 Database user
1.2 About Iris Biotech
   1.2.1 Company
   1.2.2 Products & services
   1.2.3 Statistical summary of database (percent of matches, etc.)
   A. Product order management
      1. Connect to operations server
1.4 Diagnostic/database user
   1.4.1 Request to application server
   1.4.2 Data transfer to application server
2.0 Operations Server
2.1 Product ordering management
2.2 Billing management
2.3 Order tracking management
3.0 Application Server
   3.1 Accept genetic pattern and application chip ID data from Web server
   3.2 Database query for application chip specific data
   3.3 Genetic pattern matching statistical processing
   3.4 Report generation
   3.5 Data transfer to database for particular user
   3.6 Request to database server for browse of statistical summary data
4.0 Database server
   4.1 Genome data for each application chip
   4.2 User specific data resulting from each use of an application chip
   4.3 Statistical summary of all application chip uses The system architecture is based upon suitable server(s) and/or work station(s) (e.g., servers and workstations that run on chips from Intel Corporation, IBM Corporation, or other manufacturers). Any suitable software may be used with this system (e.g., Tuxedo® software from BEA Systems Inc., and other applications). In addition, data bases may run on any suitable software that is compatible with the databases (e.g., software from Oracle Corporation, or other software).

d) System Design and Scaling

An overview of the system design and scaling is provided in FIGS. 2 and 3. The system design focuses on distributed functionality for the key functions of the system, and the associated ease of scalability when the system performance requirements increase with increasing chip sales. More specifically, the system design is based on a layered or tiered approach. This allows for system scaling with minimum impact as the system performance requirements grow. The system includes a tier for the Web server function, such as a Web Server Tier (see FIGS. 2 and 3). The Web Server Tier receives gene expression data, performs secure access function(s), allows user registration, receives and forwards test results queries, and receives and forwards transactions of gene expression data for archiving and processing. The Web Server Tier utilizes a series of low end servers (e.g., servers from Intel Corporation) to perform the user interface and data transfer functions. For the purpose of illustration, four low end servers which provide this capability are depicted in FIG. 2.

The application tier in the system performs the diagnosis processing which converts gene expression data into test results (see FIGS. 2 and 3). This tier utilizes a mid range server (e.g., E3500 Sun Enterprise server from Sun Microsystems, Inc.). This tier also performs the archiving of the gene expression data using at least one of a family of tape drive library units (e.g., Sun tape drive library unit from Sun Microsystems, Inc.). The database tier (see FIGS. 2 and 3) which performs the storage and retrieval of the test results also utilizes a mid range server (e.g., E3500 Sun enterprise server from Sun Microsystems, Inc.). This tier also utilizes a storage unit with redundancy for fault tolerance in which the test results are stored for rapid access (e.g., A5200 from Sun Microsystems, Inc.). FIG. 2 illustrates the system design in logical form.

The system design is ideal for scalability (see FIG. 3). Hence, it meets ever increasing performance requirements. The Web server tier can be "scaled horizontally" by adding additional units in parallel. The application tier can also be scaled horizontally by adding additional units in parallel. The database tier can be scaled both, horizontally with additional units in parallel (or an increased number of processors in the server), and vertically with additional storage units. This scaling concept is illustrated in FIG. 3. The scaling of any tier is independent of the scaling of any other tier. This allows maximum flexibility. For example, it is possible to scale only one tier as the system demands change with respect to combination(s) of gene expression data sets, processing throughput, test data results storage, test results queries, or the like.

e) Rules Based System

The automated artificial intelligence system of the instant invention encompasses an expert system which identifies changes to underlying assumptions for a Rules Base. The following description servers to illustrate the rules based system. It is understood, however, that the invention is not limited to the specific examples disclosed in this section.

In a rules based system, the set of rules (R) may change over period(s) of time (t).

$$R(t_0) = R_{r0}$$

$$R(t_n) = R_{rn}$$

Where $t_0$ is the creation of the rule set, and $t_n$ is the $n^{th}$ creation of the rule set.

The art describes using a mathematical or logic system as a simple set of rules to specify how to change one string of symbols into a set of symbols (J. Giarratano and G. Riley, *Expert Systems: Principles and Programming*, 2nd Edition, PWS Publishing Company, 1994, p. 30). Hence, this leads to a simple translation of data and symbol sets.

Here, x,y with Luminescence (L) Value represents a disease (D) indicator.

$$R_1 L(x,y) \chi n \rightarrow D$$

This can be translated into a conditional logic. According to Rule 1 ($R_1$), if the luminescence at x, y is $\chi$ n, then Disease (D) exists in the sample. This does not limit the order of execution(s) of rules via a control strategy.

A Markov algorithm is an ordered group of productions which are applied in order of priority to an input string (J. Giarratano and G. Riley, supra, p. 33). This allows for certain pre-tests to exist before performing the analysis to conclude that D exists.

$$R_2 L(a,b) \chi BTV \rightarrow BT(A0B)$$

Rule 2 ($R_2$) states if L at a,b is greater or equal to Blood Type Value (BTV), then Blood Type (BT) is A, 0, or B.
BT=Blood Type; BTV=Blood Type Value
Blood Type A=A
Blood Type B=B
Blood Type 0=0

The Markov algorithm allows the prioritization of the rules to be ordered. In this case, the requirement of $R_2$ to hold prioritization $P_1$ vs. $R_1$ to hold $P_2$ was not a known condition when $R_1$ was created. So,

| $P_1$ | $R_2$ | $L(a,b) \chi BTV \rightarrow BT(A0B)$ |
| $P_2$ | $R_1$ | $L(x,y) \chi n \rightarrow D$ |

The rate algorithm allows for fast pattern matching in large rule set(s) by storing information about the rules in a network. Instead of having to match facts against every rule on every recognize-act cycle, the rate algorithm only looks for changes in matches in every cycle (J. Giarratano and G. Riley, supra, p. 34). This means that the rate algorithm looks at the change or delta ($\Delta$) in patterns.

Combined with Markov algorithms, this leads to:

| $P_1$ | $R_2$ |
|  | $(\Delta P_{1,2})(\Delta R_{2,1})$ |
| $R_2$ | $R_1$ | which detects a change in the point indicator to initiate the rule if the values exist in the form of requisite values:

$$\text{if}(L(a,b)\chi BTV) \text{and}(L(x,y)\chi n) \rightarrow \text{then } D.$$

This illustrates one possible example of how to detect a change in the point indicator in order to predict any given disease. However, the system is flexible and adapts to new rules, thus:

$$R_1 \neq R_2 \neq R_n$$

And the priority/prioritization (P) for execution may change in each rule set, representing a transform (TR) in the prioritization of the data represented in rules.

Thus, Transform (TR) Priority (P) may exist at a given time (t), so that:

$$TR(P(t))$$

and $$TR(P(1)) \neq TR(P(2)) \neq TR(P(3))$$

Generally, the rate algorithm tracks only the changes, but does not group classes of changes or identify root causes behind changes. Thus, new rules may be applied to group classes of changes or identify root causes behind changes.

$$(\Delta P_{1,2})(\Delta R_{2,1}) \rightarrow D$$

It is also relevant to identify and track additional information and call these pieces of additional information assumption (A), for example, ($A_t$):

$$A_1 \Rightarrow L(a,b) \Rightarrow BTV \text{ of}(A,B)$$

$$A_2 \Rightarrow L(a,b) \Rightarrow BTV \text{ of}(A,0,B)$$

In a dynamic application it may be necessary to determine what the underlying assumptions to the valid data and/or result sets are. This may influence the potential entry point(s) for analysis and may indicate a need to preprocess or reprocess data against multiple rules for describing test results.

Results 1:

| $P_1$ | $R_2$ | $A_1$ | $\Rightarrow$ |  |
| $R_2$ | $R_1$ | $A_1$ | $\Rightarrow$ | D |

Results 2:

| $P_1$ | $R_2$ | $A_2$ | $\Rightarrow$ |  |
| $R_2$ | $R_2$ | $A_2$ | $\Rightarrow$ | not D |

Providing Results 2 (with $A_2$) in order to describe the underlying root cause for results conveys more information to the user. Providing both sets of results as well as describing the differing results to the user may assist in developing trend data in a population set. For example, examining a population segment may provide information about several individuals reporting symptoms of low energy and out-of-breathness at time $t_{(1)}$, $t_{(2)}$, $t_{(3)}$, and $t_{(4)}$. A medical break-through occurs between $t_{(4)}$ and $t_{(5)}$, identifying the symptoms of disease $D_5$.

| $T_1$ | $P_1$ | $R_1$ | $A_1$ | $\Rightarrow$ | $0 D_5$ |
| $T_2$ | $P_2$ | $R_2$ | $A_1$ | $\Rightarrow$ | $0 D_5$ |
| $T_3$ | $P_3$ | $R_3$ | $A_1$ | $\Rightarrow$ | $0 D_5$ |
| $T_4$ | $P_4$ | $R_4$ | $A_1$ | $\Rightarrow$ | $0 D_5$ |
| $T_5$ | $P_5$ | $R_5$ | $A_5$ | $\Rightarrow$ | $D_5$ |

In the illustration above, the rate algorithm accounts for a change in the rules, but does not identify a change or delta (A) in the underlying assumptions.

The above rules based decision making process is only an example and servers to illustrate one embodiment of the instant invention. In an alternative embodiment of the instant invention, neural networks may be used to accomplish the above illustrated objectives. In yet another alternative embodiment of the instant invention, other application(s) may be employed.

f) Image Processing Software

The image processing software hosted in the PC's attached to the genetic profiling microarrays systems deployed at user sites may or may not be an element of the artificial intelligence system. The image processing software provides image data from test data for use in the artificial intelligence system. The key function of the image processing software is to generate an intensity level for each spot on the chip for each fluorescent color used. The intensity data is normalized to both positive and negative control spots on the chip, thus it defines gene expression levels. The data generated by the image processing software is then sent to the central processing facility of the artificial intelligence system for analysis. Comparative hybridization may also be used. There are several existing image processing applications that can be used for microarray test data image processing. Examples are the software associated with the GenePix™ 4000 scanner from Axon Instruments, Inc., the software associated with the Scan Array® 5000 scanner from GSI Lumonics, and others. Stand alone microarray test data image processing software tools are optionally employed. Examples include the IPLab in the Microarray Suite from Scanalytics Inc., and ImaGene™ from Bio Discovery, Inc. The selection of image processing software is usually selected based on the scanner system used. Alternatively, any image processing software that is compatible with the scanner system may be employed. Optionally, a custom scanner or Charged Coupled Device (CCD) based system is available in conjunction with the artificial intelligence system.

g) Examples

The following specific examples are intended to illustrate the invention and should not be construed as limiting the scope of the claims. The examples further illustrate some of the specifics within the artificial intelligence system and factors that effect how the system is used.

I. Integration of Public Databases (DBs) into the Database (DB) of the Artificial Intelligence System.

The following databases, databanks, information sources, and data are integrated into the system of the instant invention, wherein information is stored, downloaded, and upgraded routinely.

National Center for Biotechnology Information (NCBI)
$\Rightarrow$ GenBank
$\Rightarrow$ UniGene
$\Rightarrow$ GeneMap
$\Rightarrow$ EST, STS, and SNP Database(s)
Online Mendelian Inheritance in Man Database (OMIMT™)
$\Rightarrow$ Diseases and Mutations
$\Rightarrow$ Blast Engine(s)
$\Rightarrow$ Others
National Library of Medicine (NLM)
$\Rightarrow$ Centers for Disease Control and Prevention(CDC)
$\Rightarrow$ Federal Drug Administration (FDA)
$\Rightarrow$ National Institute(s) of Health (NIH)
$\Rightarrow$ others II. Data Mining from Public Information The artificial intelligence system allows for data mining which includes mining for information such as:
$\Rightarrow$ Current research and development on genetic and medical sciences
$\Rightarrow$ New technologies (array technologies, diagnostic tools, drug development, genetics testing, high throughput screening, etc.)
$\Rightarrow$ Market information (domestic and international, basic research and clinical applications)
$\Rightarrow$ Competitor information
$\Rightarrow$ Political, economic, social (life style, healthcare, etc.) trends and changes III. Information for Major Decisions The artificial intelligence system provides information related to the following:

General Information

This information is related to management strategic decision(s), company direction(s), finance(s), market targeting, and others.

Specific Information

This information is related to project decision(s), technology application(s), research & development, product design, gene selection, and others. Information is correlated and integrated into the artificial intelligence system. The information is:
$\Rightarrow$ Market based
$\Rightarrow$ Disease based
$\Rightarrow$ Technology based
$\Rightarrow$ Species based
$\Rightarrow$ Function based
$\Rightarrow$ Pathway based
$\Rightarrow$ Sequence based
$\Rightarrow$ Mutation based
$\Rightarrow$ Cluster based Disease-; Gene-, and Sequence Analysis Information This analysis information is organized and stored in various databanks:
$\Rightarrow$ Disease gene(s) classification: Disease Databank
$\Rightarrow$ Pathway, interaction(s), and regulation(s) network: Pathway Databank
$\Rightarrow$ Clusters and their unique regions: Cluster Databank
$\Rightarrow$ Sequencing and oligonucleotide design: Oligo Databank
$\Rightarrow$ Mutations: Mutation Databank IV Organization of Genetic Materials Genetic Materials are organized in a Gene Databank, wherein this databank includes, but is not limited to:
$\Rightarrow$ Gene selection
$\Rightarrow$ Materials preparation or synthesis
$\Rightarrow$ Materials coding
$\Rightarrow$ Materials storage
$\Rightarrow$ Materials tracking

V. Gene Selection

Specific computer program(s) are used in order to select genes of interest within the database(s). Thus, in selecting genes or segment(s) of genes to represent a particular gene, various computer programs are employed. For example, a computer program may be used to select genes such as BRCA1, BRCA2, HER2/neu, p53, and p57 as genes of interest to be put/added onto a Breast Cancer Gene Chip. For the BRCA1 gene, another computer program may be used to select one or more unique 50 mer oligo sequence(s) with the desired GC content, minimal hairpin formation, minimal dimer formation, and optimal melting temperature.

VI. Preparation of Genetic Materials

The preparation of genetic materials includes, but is not limited to:
⇒ High throughput amplification and purification
⇒ Oligo/peptide nucleic acid (PNA) design
⇒ Oligo/peptide nucleic acid (PNA) synthesis
⇒ Sequencing confirmation
⇒ Concentration adjustment

VII. Microarray Design and Tracking

Microarrays are designed and tracked via an Array Databank, wherein this databank includes, but is not limited to:
⇒ Array design (e.g., artificial intelligence (AI); controls; programmed image(s); grouped by disease(s), function(s), pathway(s); underlying network; phenotype-genotype correlation; and others)
⇒ Array location ID in conjunction with genetic materials information, sample ID storage plates, and other parameters
⇒ Array ID connected to final imaging, data analysis and data export to end users

VIII. Spotting

Spotting encompasses inkjet printing system calibration(s) and monitoring of key parameters.

IX Tissue

Tissue that is being tested is tracked and recorded in a Sample Databank. All tested tissues are recorded with respect to the following parameters:
⇒ Sources: people/animal/other
⇒ Tissue type: e.g., blood, breast tissue, liver tissue, etc.; normal tissue, diseased tissue, compromised tissue, tumor tissue, stressed tissue, etc.
⇒ Diagnosis before testing
⇒ Treatment or test before genetic profiling microarray testing
⇒ Control sample information
⇒ Tissue preparation information/labeling procedure
⇒ Other

X Hybridization

Hybridization information includes, but is not limited to:
⇒ Programmed hybridization procedure(s) in conjunction with fluidic station(s)
⇒ Hybridization condition(s) (e.g., buffer component, time cycle, temperature control, etc.)
⇒ Washing
⇒ Chip storage

XL Results Analysis

The results analysis is divided into three stages, such as:
Image Analysis: Image Databank
⇒ Translate real image to analytical image
⇒ Transfer image to digital/number (pixel intensity)
⇒ Sorting, regrouping, comparing, filtering and highlighting significant changes
⇒ Correlating to public and internal data
⇒ End user communication Profiling: Profile Databank
Expression profile by different tissues, diseases, ethnic groups, treatments, pathway, genes, etc.
Mutation and Disease: Mutation Databank
Mutation DB: disease types, phenotype-genotype correlations

XII. Information Presented through a User Interface

The artificial intelligence system provides information to the user, through a network (e.g., Internet) via a user interface. Information is presented through windows, screens, menus and the like, which allow the user to conveniently view user information, clinical sample information, testing information, clinical test results report, R&D sample information, chip information, results report for biopharma chip, therapeutic choices, billing information, and others.

The following are examples of information presented to the user via the user interface:
User Information
User ID (user specific/secured)
Password (user specific/secured)
⇒ Name
⇒ Sex
⇒ Date of Birth
⇒ Ethnicity
⇒ Social Security Number (SSN)
⇒ Health History Occupation
⇒ Employer Information
⇒ Insurance Information
⇒ Physician's Information/Clinic & Hospital Information
⇒ Family History
⇒ Diagnosis
a) Clinical/Physician
b) Pathology
c) Clinical/Lab
d) Genetic Test
Clinical Sample Information
Date
⇒ Sample ID
⇒ Patient ID
⇒ Organ
⇒ Tissue
⇒ Cell
⇒ DNA or mRNA
⇒ Preparation/Amplification/Purification
⇒ Labeling
⇒ Storage
⇒ Control Sample Information
Testing Information
Date of the Test
Type of Testing
⇒ Genetic Testing
⇒ Expression Profile
Classified Testing
⇒ Cancer
⇒ Cardiovascular
⇒ Neurological
⇒ Endocrinological
⇒ Infectious
⇒ Metabolic
⇒ Hematological
⇒ Immunological
⇒ Aging
Chip Used
Hybridization Method(s) & Condition(s)
Clinical Test Result Report
Date
Chip ID Patient ID
Sample ID
Genetic Testing
⇒ Mutation
⇒ Amplification
Expression Profile
⇒ Abnormal Expression Pattern
⇒ Related Genes
R&D Sample Information
Source of the Samples
⇒ Human
⇒ Animal
⇒ Insect
⇒ Viral
⇒ Bacterial
⇒ Yeast
⇒ Agricultural
⇒ Others
Tissue(s) and Cell Type
Treatment
⇒ Reagent(s)
⇒ Concentration
⇒ Time Period
⇒ Specific Treatment
Sample Preparation Information
Labeling, Storage, and Hybridization Information Control
Chip Information
Chip ID
Type of Chip
⇒ BioPharma
⇒ Custom Made (R&D)
⇒ Clinical
Chip Classification
⇒ Disease Specified
⇒ Function Specified
⇒ Mutation Related
Complete Probe Information
Complete Array Information
Direct Link of the Information to Genetic Database
Result Report for BioPharmaChip
Type of Experiment(s)
⇒ Expression
⇒ Mutation
⇒ Amplification
Chip Classification
⇒ Disease Based
⇒ Functionality Based
Structure Based
Top Hit List (e.g., Top 10 Hits, Top 100 Hits, etc.)
⇒ Over Expressed and Under Expressed Genes Compared with Controls
⇒ Mutations Generated or Detected
⇒ Genomic Amplification
Conclusions by Researcher(s), Physician(s), Genetic Counselor(s), etc.
Therapeutic Choices
⇒ Patient ID
⇒ Sample ID
⇒ Chip ID
⇒ Test Result and Diagnosis: Disease vs. Genotype/Expression Alterations
⇒ Available Therapeutics
⇒ Alternative Therapeutic Choices
⇒ Therapeutics under Development
Billing Information
⇒ Patient ID or Customer ID
⇒ Sample ID
⇒ Chip ID
⇒ Test Result
⇒ Insurance Billing Information
⇒ Doctor Fee
a) Reimbursement by Insurance Company
⇒ Patient Payment
⇒ Customer Payment XIII. Online Marketing, Ordering and Shipping System (B2B2C)

The artificial intelligence system includes an operations server which stores information regarding orders, billing, order tracking, shipping, and others. E-commerce related information is also provided. E-commerce transactions may include patient(s) purchasing prescription drug(s); insurance companies offering discount(s) to individual(s) with healthy Genetic Profiles (GPs); farmer(s) purchasing new Genetically Modified Organisms (GMOs); user(s) subscribing to specific news bulletin(s); and user(s) ordering specific book(s) or other information material to help them understand specific genetic profile(s). The system also optionally includes educational information/seminar(s), and specific chat room(s) and gathering(s) of support groups on-line that may attract large number(s) of regular visitors, offering further advertisement options and facilitation of commerce involving a wide variety of products and services.

XIV. End User Application

The end user application includes the following:
⇒ Windows based platform
⇒ Firewall protected entry
⇒ User password (PW) and sample ID specified log-on
⇒ Selected and limited access by diagnostic user and browse user
   ⇒ Online technical support system(s)

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the claims.

What is claimed is:

1. An artificial intelligence system for the analysis of gene or protein expression information related to an individual patient for determining a physiological condition of said patient, said system comprising:
   an application server that is configured to analyze said gene or protein expression information through the use of an algorithm adapted for:
      performing an analysis step comprising one or both of:
         i) analyzing gene expression levels associated with a plurality of genes of the patient, and
         ii) analyzing protein expression levels associated with a plurality of proteins of the patient,
      relating said gene expression levels or protein expression levels with patient personal medical history of said patient, and
      determining a likelihood of said patient developing a specific disease based on said related gene expression levels or protein expression levels and patient personal medical history.

2. The system of claim 1, further comprising a Web server that is configured to perform a function selected from the group consisting of receiving expression information related to said patient, transmitting expression information related to said patient, supporting data analyses, providing security and business functions, receiving or transmitting product information, product ordering, providing a statistical summary of patient database, and providing a request to the application server.

3. The system of claim 1, further comprising a database server that is configured to perform a function selected from the group of functions consisting of storing hybridization profiles, storing clinical information associated with hybridization profiles, storing personal medical history information related to the patient, storing treatments suitable for diagnosed conditions related to hybridization profiles, and storing statistical information associated with hybridization profiles; wherein data stored by the database server further comprises one or more of data selected from the group consisting of genetic pattern database data for chip identification, patient genetic pattern database data, and statistical data summary data.

4. The system of claim 1, further comprising a Web server and a database server, wherein the application server constructs at least one query for the database server, and performs at least one statistical comparison between expression information received by the Web server and expression information supplied by the database server.

5. The system of claim 4, wherein the application server is further configured to perform one or more functions selected from the group of functions consisting of database query for chip identification, database query for genetic pattern, database query for statistical data summary, pattern match statistical processing, and results output.

6. The system of claim 1, wherein said artificial intelligence system further comprises an operations server.

7. The system of claim 6, wherein the operations server comprises functions selected from the group consisting of order management, billing management, and order tracking.

8. The system of claim 1, further comprising a user facility configured to provide expression information, wherein the user facility is linked to said artificial intelligence system through encrypted network connections.

9. The system of claim 1, wherein the application server is further configured to provide a diagnosis of a physiological condition of the patient suggested by the algorithm.

10. The system of claim 1, wherein the application server further comprises a rules based system including one or more of: conditional logic, prioritization, pattern matching, detection of changes in matches, detection of changes in a pattern, detection of changes in a disease indicator, development of trend data in a population set, adaption of assumptions, and adaption of rules.

11. The system of claim 9, wherein the application server is further configured to provide recommendation for methods of treatment for said patient based on the diagnosed physiological condition.

12. The system of claim 8, wherein the user facility comprises:
an image processing system to convert optical data from an optical scanning system into a set of expression parameters,
a computer linked to a network; and
a user interface to display data related information.

13. The system of claim 12, wherein the network is the Internet.

14. The system of claim 12, wherein the user interface further comprises functions selected from the group of functions consisting of manipulating data, searching data, analyzing data, and displaying data.

15. The system of claim 14, wherein the user interface further comprises displayed information selected from the group consisting of user information, clinical sample information, testing information, clinical test results report, research and development sample information, chip information, results report for biopharma chip, therapeutic choices, and billing information.

16. The system of claim 12, wherein the data related information is selected from the group consisting of expression information, patient information, statistical information, clinical information, medical information, diagnosis information, treatment information, biological information, product information, and company information.

17. The system of claim 12, wherein the user facility further comprises a function selected from the group consisting of genetic pattern processing, request for pattern match for chip identifier, and report generation.

18. The system of claim 8, wherein the user facility comprises:
a computer linked to a network; and
a user interface to display data related information.

19. The system of claim 18, wherein the data related information comprises data selected from the group consisting of expression information, patient information, statistical information, clinical information, medical information, diagnosis information, treatment information, biological information, product information, and company information.

20. The system of claim 1, comprising a system architecture based on a shared processing functionality between at least one remote location and at least one central data processing facility.

21. A method for diagnosing a physiological condition of an individual patient, comprising:
analyzing gene or protein expression information related to said patient, to generate an expression profile related to said patient, the analysis comprising one or both of:
analyzing gene expression levels associated with a plurality of genes of the patient, and
analyzing protein expression levels associated with a plurality of proteins of the patient,
relating said expression profile to one or more of stored expression parameters, stored disease models, profiles from other patients, and stored patient medical history information and clinical observations related to said patient, and
diagnosing a probable physiological condition based on said related expression profile and said one or more of stored expression parameters, stored disease models, profiles from other patients, and stored patient medical history information and clinical observations related to said patient.

22. The method of claim 21, further comprising updating said stored expression parameters and said stored patient medical history to include one or more of said expression information, said expression profile, said diagnosed probable physiological condition, and a recommended method of treatment.

23. The method of claim 21, further comprising recommending methods of treatment for said patient based on the diagnosed physiological condition, patient personal medical history and clinical observations.

24. The method of claim 21, wherein said diagnosis of a probable physiological condition is performed by an algorithm comprising a rules based system including one or more of conditional logic, prioritization, pattern matching, detection of changes in a pattern, detection of changes in a disease indicator, development of trend data in a population set, adaption of assumptions, and adaption of rules.

25. A method for diagnosing a physiological condition of a living organism, comprising:
analyzing gene or protein expression information related to said living organism, to generate an expression profile related to said living organism, the analysis comprising one or both of:
analyzing gene expression levels associated with a plurality of genes of the organism, and
analyzing protein expression levels associated with a plurality of proteins of the organism,
relating said expression profile to one or more of stored expression parameters, disease models and living organism profiles, and
diagnosing a probable physiological condition based on said related expression profile and said one or more of stored expression parameters, disease models and living organism profiles.

26. The method of claim 25, further comprising updating one or both of said stored expression parameters and said living organism profiles.

27. The method of claim 25, wherein the living organism is an animal.

28. The method of claim 25, wherein the living organism is a plant.

29. The method of claim 23, wherein said diagnosis of a probable physiological condition is performed by an algorithm comprising a rules based system including one or more of conditional logic, prioritization, pattern matching, detection of changes in matches, detection of changes in a pattern, detection of changes in a disease indicator, development of trend data in a population set, adaptation of assumptions, and adaptation of rules.

30. The method of claim 25, wherein said diagnosis of a probable physiological condition is performed by an algorithm comprising a rules based system including one or more of conditional logic, prioritization, pattern matching, detection of changes in matches, detection of changes in a pattern, detection of changes in a disease indicator, development of trend data in a population set, adaptation of assumptions, and adaptation of rules.

31. The method of claim 25, further comprising recommending methods of treatment for said living organism based on the diagnosed physiological condition, disease models, and living organism profiles.

32. The artificial intelligence system of claim 1, further comprising relating said gene expression levels or protein expression levels with patient family history to determine a likelihood of developing a specific disease.

33. The method of claim 21, further comprising relating said gene expression levels or protein expression levels with patient family history to determine a likelihood of developing a specific disease.

34. The system of claim 1, wherein the system is a stand-alone system that interfaces directly with a central data processing facility.

35. An artificial intelligence system for analysis of gene or protein expression information related to an organism, said system comprising:
a computer system that is configured to analyze said gene or protein expression information through the use of an algorithm adapted for:
performing an analysis step comprising one or both of:
i) analyzing gene expression levels associated with at least one gene of the organism, and
ii) analyzing protein expression levels associated with at least one protein of the organism,
relating said gene expression levels or protein expression levels with a biological history of said organism, and
based on said related gene expression levels or protein expression levels to said history, performing a step comprising one or more of:
i) determining a likelihood of said organism developing a specific disease,
ii) detecting a disease of said organism,
iii) providing a prognosis for said organism,
iv) providing a diagnosis for said organism, and
v) recommending or providing information for recommendation of a treatment.

* * * * *